(12) United States Patent
Riordan

(10) Patent No.: US 7,749,495 B2
(45) Date of Patent: Jul. 6, 2010

(54) METHOD FOR INDUCING AN ANTI-TUMOR AND ANTI-CACHEXIA IMMUNE RESPONSE IN MAMMALS

(75) Inventor: Neil H. Riordan, Chandler, AZ (US)

(73) Assignee: Aidan, Inc., Tempe, AZ (US)

( * ) Notice: Subject to any disclaimer, the term of this patent is extended or adjusted under 35 U.S.C. 154(b) by 0 days.

(21) Appl. No.: 12/126,744

(22) Filed: May 23, 2008

(65) Prior Publication Data
US 2008/0219958 A1  Sep. 11, 2008

Related U.S. Application Data

(60) Division of application No. 10/871,340, filed on Jun. 18, 2004, now abandoned, which is a continuation of application No. 09/781,023, filed on Feb. 9, 2001, now abandoned.

(60) Provisional application No. 60/226,752, filed on Aug. 21, 2000.

(51) Int. Cl.
  A61K 35/14 (2006.01)
  A61K 35/12 (2006.01)
(52) U.S. Cl. ............... 424/93.7; 424/93.1; 424/93.21
(58) Field of Classification Search .................. None
  See application file for complete search history.

(56) References Cited

U.S. PATENT DOCUMENTS 5,643,786 A    7/1997  Cohen
7,557,193 B2 *  7/2009  Lombardo et al. ....... 530/388.1

FOREIGN PATENT DOCUMENTS

DE  197 24 546 A1  12/1997
EP   335 550 A1  10/1989

OTHER PUBLICATIONS

BMJ, Editorials, 1999;318:208-209 (Jan. 23).*
Hegyeli et al. Science Dec. 20, 1963: vol. 142, pp. 1571-1572.*
Cariuk, et al. 1997. Induction of cachexia in mice by a product isolated from the urine of cachectic cancer patients. *British Journal of Cancer*, 76(5):606-613.
Chawla, et al. 1997. Isolation and characterization of a glycoprotein (JBB5) in theuUrine of a patient with carcinoma of the colon. *Cancer Research*, 37:873-878.
Cohen, et al. 1994. CD4+ T-Cells from mice immunized to syngeneic sarcomas recognize distinct, non-shared tumor antigens. *Cancer Research*, 54:1055-1058.
Curti, B. D. 1993. Physical barriers to drug delivery in tumors. *Critical Reviews in Oncology/Hematology*, 14:29-39.
DeVere White, et al. 1992. Urinary prostate specific antigen levels: Role in monitoring the response of prostate cancer to therapy. *The Journal of Urology*, 147:947-951.
Eldor, J. 1997. Urotherapy for patients with cancer. *Medical Hypotheses*, 48:309-315.

Euhus et al. 1989. Detection of a tumor-associated glycoprotein antigen in serum and urine of melanoma patients by murine monoclonal antibody (AD1-40F4) in enzyme immunoassay. *Journal of Clinical Laboratory Analysis*, 3:184-190.
Ezzell, C. 1995. Cancer "vaccines": An idea whose time has come? *The Journal of NIH Research*, 7:46-49.
Finck et al. 1982. Excretion of tumor-associated antigen(s) in the urine of patients with colon carcinoma. *Journal of Surgical Oncology*. 21:81-86.
Geiger, et al. 2001. Vaccination of pediatric solid tumor patients with tumor lysate-pulsed dendritic cells can expand specific T cells and mediate tumor regression. *Cancer Research*, 61:8513-8519.
Green, S. B. 1982. Patient heterogeneity and the need for randomized clinical trials. *Controlled Clinical Trials*; 3:189-198 (abstract only).
Gura, T. 1997. Systems for identifying new drugs are often faulty. *Science*, 278:1041-1042.
Halberg, at al. 1995. Cancer marker assessment: Case report on salivary and urinary CEA. in vivo, 9:311-314.
Hartwell, et al. 1997. Integrating genetic approaches into the discovery of anticancer drugs. *Science*, 278:1064-1068.
Herbert, V. 1986. Unproven (questionable) dietary and nutritional methods in cancer prevention and treatment. *Cancer*, 58(8 Suppl):1930-1941 (abstract only).
Hsu, et al. 1996. Vaccination of patients with B-celllymphoma using autologous antigen-pulsed dendritic cells. *Nature Medicine*, 2(1):52-58.
Jain, R. K. 1994. Barriers to drug delivery in solid tumors. *Scientific American*, 271(1):58-65.
Morales, et al. 1995. Immunotherapy of an experimental adenocardinoma of the prostate. *The Journal of Urology*, 153:1706-1710.
Morton, et al. 1992. Prolongation of survival in metastatic melanoma after active specific immunotherapy with a new polyvalent melanoma vaccine, *Ann. Surg.*, 216(4):463-482.
Murphy, et al. 1996. Phase I clinical trial: T-Cell therapy for prostate cancer using autologous dendntic cells pulsed with HLA-A0201L-specific peptides from prostate-specific membrane antigen. *The Prostate*, 29:371-380.
Nestle, et al. 1998. Vaccination of melanoma patients with peptide- or tumor lysate-pulsed dendritic cells. *Nature Medicine*, 4(3)328-332.
Raschetti, R., BMJ. Jan. 23, 1999; 318(7178):224-228.
Ravery, V. 1999. The significance of recurrent PSA after radical prostatectomy: Benign versus malignant sources. *Seminars in Urologic Oncology*, 17(3):127-129.
Rote, et al. 1980. Determination of incidence and partial characterization of tumor-associated antigens found in the urine of patients bearing solid tumors. *Int. J. Cancer*, 26:203-210.

(Continued)

*Primary Examiner*—Misook Yu
(74) *Attorney, Agent, or Firm*—Knobbe Martens Olson & Bear LLP

(57) ABSTRACT

The invention relates to inducing an immune response toward tumor associated antigens and in particular to the administration of high molecular weight isolates of autologous urine either alone, with adjuvants, or with antigen presenting cells. The antigen presenting cells have been cocultured with isolates of autologous urine. The invention can also be used to treat cachexia in cancer or AIDS patients.

22 Claims, No Drawings

OTHER PUBLICATIONS

Spitler, L. E. 1995. Cancer vaccines: The interferon analogy. *Cancer Biotherapy*, 10(1):1-3.

Voet, et al. 1990. *The urea cycle*. In Biochemistry, Sec. 24-2, p. 682. New York: John Wiley & Sons.

Yedavelli, et al. 1999. Preventive and therapeutic effect of tumor derived heat shock protein, gp96, in an experimental prostate cancer model. *International Journal of Molecular Medicine*, 4:243-248.

Younes, et al. 2000. Pathophysiology of cancer cachexia. *Rev. Hosp. Clin. Fac. Med. S. Paulo*, 55(5):181-193.

Zitvogel, et al. 1998. Eradication of established murine tumors using a novel cell-free vaccine: Dendritic cell-derived exosomes. *Nature Medicine*, 4(5):594-600.

\* cited by examiner

METHOD FOR INDUCING AN ANTI-TUMOR AND ANTI-CACHEXIA IMMUNE RESPONSE IN MAMMALS

RELATED APPLICATIONS

This application is a divisional of U.S. patent application Ser. No. 10/871,340, entitled METHOD FOR INDUCING AN ANTI-TUMOR AND ANTI-CACHEXIA IMMUNE RESPONSE IN MAMMALS, filed Jun. 18, 2004, which is a continuation of U.S. patent application Ser. No. 09/781,023, entitled METHOD FOR INDUCING AN ANTI-TUMOR AND ANTI-CACHEXIA IMMUNE RESPONSE IN MAMMALS, filed Feb. 9, 2001, which claims priority under 35 U.S.C. §119(e) to U.S. Provisional Patent Application Ser. No. 60/226,752, entitled METHOD FOR INDUCING AN ANTI-TUMOR AND ANTI-CACHEXIA IMMUNE RESPONSE IN MAMMALS, filed Aug. 21, 2000, each disclosure of which is incorporated herein by reference in its entirety.

FIELD OF THE INVENTION

The invention relates to inducing an immune response toward tumor associated antigens and in particular to the administration of isolates of autologous urine either alone, with adjuvants, or with antigen presenting cells which have been co-cultured with isolates of autologous urine.

BACKGROUND OF THE INVENTION

The treatment of disseminated cancer is a problem for clinical and veterinary medicine. The treatment regimens available today include surgery, radiation, chemotherapy, and immunotherapy. Surgery often fails due to tumor tissue which is unrecognized and not removed. Radiation and chemotherapy also fail, and the side-effects of the treatments often decrease the quality of life of the patients.

The major benefit offered by immunotherapy is that it is not generally associated with the side effects of surgery, radiation or chemotherapy. In three recent studies using dendritic cell immunotherapy in patients with cancer, minimal to no side effects were reported (Hsu, et al. Nature Medicine, 1996 2:52-58; Murphy, et al. The Prostate, 1996 29:371-380; Nestle, et al. Nature Medicine, 1998, 4 (3):328-332).

Immune therapy for cancer has been employed for many years. One of the first immune treatments was a mixed bacterial vaccine. More recently, mixtures of irradiated malignant melanoma cells have been used to induce immune responses in patients with malignant melanoma, which increased survival in several patients (Morton, et al. Ann. Surg. (1992) 216:463-482).

Newer immunotherapeutic strategies are directed toward enhancing T-lymphocyte specific immune responses toward tumors. Some strategies use genetically altered tumor vaccines, and others use non-altered antigen presenting cells to present tumor antigens to lymphocytes.

Antigen presenting cells (APCs) are naturally occurring cells which have the capability to present "foreign" and "self" antigens (proteins) to the immune system. Effective presentation of antigen to the immune system can activate T lymphocytes to fight infection and cancer. Typically, antigens which are either a part of a protein (eg. a peptide), or whole pieces of protein are co-cultured with and transferred to the APCs (Cohen P. A. et al 1994 *Cancer Res* 54:1055-1058), a method commonly referred to as "pulsing."

The dendritic cell (DC) is one type of antigen presenting cell. DCs are present in small numbers in most tissues including skin, liver, lung, spleen, blood, lymphoid organs, peripheral blood, and bone marrow (Hsu F J, et al. Nature Med, 1996 2:52-58).

DCs pulsed with proteins are capable of presenting processed antigen to lymphocytes for days. After being pulsed with tumor antigen, autologous DCs have been re-infused into patients, and induced partial tumor regression in some prostate tumor patients, and lymphoma patients (Murphy G, et al. The Prostate, 1996 29:371-380, Hsu F J, et al. Nature Med, 1996 2:52-58).

Protocols have been developed to isolate and purify DCs from human blood. Three approaches used to date include:

1. Isolating bone marrow precursor cells from the blood, and stimulating them to differentiate into DCs and grow in large numbers (Romani N, et al 1994 *J Exp Med*, 180:83-93; Romani N et al. 1996 *J Immunol Methods;* 196(2):137-51 and; Reddy et al. 1997, *Blood;* 90(9): 3640-6).
2. Collecting precommitted DCs from peripheral blood (Greudenthal P. S. et al 1990 *Proc Natl Acad Sci* 87:7698-7702; Mehta-Damani, et al. 1994 *J Immunol* 153:996-1003; Thomas R. et al. 1993 *J. Immunol* 151: 6840-6852; and Cohen P A et al, 1997, U.S. Pat. No. 5,643,786).
3. Inducing conversion of leukapheresed monocytes using calcium ionophore (U.S. Pat. No. 5,643,786 July 1997 Cohen).

The use of the proper tumor antigen to pulse DCs can predict the success of DC-based immunotherapy. In a recent study (Murphy G. et al. *The Prostate,* 1996 29:371-380) prostate cancer patients were treated with dendritic cells pulsed with an HLA-A0201 (a subset of HLA-A2 family)-specific prostate-specific membrane antigen peptide. The only patients who responded favorably to the treatment were those who expressed the HLA-A2 antigen. In another study of DC therapy in patients with B-cell lymphoma (Hsu F J et al. *Nature Med,* 1996 2:52-58), the antigens used to pulse DCs were idiotype proteins derived from cell fusion techniques using tumor biopsies as starting materials. Both treatment methods have shortcomings. In the case of the prostate tumor treatment, the antigen is useful only in HLA-A2+ patients. In the lymphoma treatment, the process of isolation of biopsy tumor material and cell-fusion techniques are both difficult and may be impossible in many patients. Use of a singular priming antigen to pulse the DCs could also lead to escape variant tumor cell types.

Many tumor associated antigens have been identified, and an epitope of at least one tumor antigen has been used successfully to pulse dendritic cells which resulted in partial responses in prostate cancer patients (Murphy et al. The Prostate, 1996 29:371-380). Some are used as tumor markers and rising levels can be indicative of disease progression.

Very high molecular weight (>1,000,000 daltons) tumor associated antigens have been found in the urine of 94.7% of patients with many types of cancer (Rote N S et al. 1980 *Int. J. Cancer* 26:203-210). Other high molecular weight tumor associated molecules have been found in the urine of cancer patients. Researchers (Chawla R K et al. 1977, Cancer Res 37:873-878) reported the presence of a glycoprotein (51,000 to 59,000 daltons) in the urine of 64% of colon cancer patients which could not be detected in the urine of non-cancer patients, but was found in the urine of 15-50% of patients with other various advanced malignancies. Another group found a >100,000 daltons molecular weight tumor-associated antigen in the urine of 65.4%-71.4% of colon cancer patients which was not detectable in 90% of healthy volunteers (Finck S J et al. 1982. *J. Surg. Oncology* 21:81-86). A tumor associated antigen having a molecular weight of 590,000-620,000 daltons was found in the urine of 68% of melanoma patients as opposed to 5% of normal controls (Euhus D M et al. 1989, *J Clin Lab Anal* 3:184-190). Prostate Specific Antigen (PSA), a 34,000 dalton molecular weight glycoprotein has been found in the urine of prostate cancer patients (deVere White R W, et al, 1992; J Urol. 147:947-951). Carcinoembryonic antigen (CEA), a high molecular weight (200,000 to 240,000 daltons) tumor marker associated with gastrointestinal tumors, has also been found in the urine of cancer patients (Halberg F, et al. 1995 *In Vivo* July-August; 9 (4):311-4).

Another protein (24,000 daltons) that is capable of inducing cachexia in mice has recently been found in the urine of cancer patients (Cariuk P, et al. 1997 *Br J Cancer;* 76:606-13). The antigen was not present in the urine of normal subjects, patients with weight loss from conditions other than cancer, or from cancer patients who were weight stable or with low weight loss (1 kg month(−1)). The antigen was present in the urine from subjects with carcinomas of the pancreas, breast, lung and ovary. The protein-induced cachexia in mice can be reversed by the administration of a monoclonal antibody to the protein to the mice.

The above list of tumor associated antigens is not complete. Other tumor associated antigens are being discovered yearly. Identification, purification, and characterization of these antigens is costly and time consuming. Until now, no tumor associated antigen with 100% specificity and sensitivity has been identified.

The ability of a high molecular weight isolate of autologous urine to stimulate anti-tumor and anti-cachexia responses was studied herein. In one embodiment the effects of dendritic cells that had been pulsed (by co-culturing and by induction of pinocytic inclusion through osmotic lysis) with a high molecular weight isolate of autologous urine (without identification, purification, or characterization of tumor associated antigens) from humans with metastatic disease was studied. As part of this investigation, it was discovered that the injection of dendritic cells pulsed with a high molecular weight isolate of urine from humans with metastatic disease did not cause any side-effects, including autoimmune diseases, when reinfused into the patient. It was also found that these dendritic cells were capable of:

1. Inducing T lymphocyte mediated cytotoxicity of human tumor cells in vitro;
2. Inducing T lymphocyte proliferation in vitro;
3. Inducing lymphocyte stimulation detected by increased interferon-gamma production in vitro; and,
4. Halting cachexia in a patient with metastatic prostate carcinoma when intravenously infused.
5. Shrinking the tumor of a patient with a large intracranial neuroblastoma.

SUMMARY OF THE INVENTION

It is therefore one purpose and object of the present invention to stimulate an anti-cancer immune response in a mammal with cancer using injections of high molecular weight autologous urine isolates containing tumor associated antigen(s) with or without the use of adjuvants. It is a further purpose of the present invention to stimulate an anti-cachexia immune response in a mammal with cancer or AIDS using injections of high molecular weight autologous urine isolates containing cachexia-inducing molecules with or without the use of adjuvants. It is a further purpose of the present invention to stimulate an anti-cancer immune response in a mammal with cancer by the injection of antigen presenting cells that have been treated with high molecular weight autologous urine isolates containing tumor associated antigen(s). It is another purpose of the present invention to halt cachexia in mammals with cancer by the injection of antigen presenting cells that have been treated with high molecular weight autologous urine isolates.

In its broadest aspect, the invention provides a method of treating cancer in a mammal in need of such treatment which comprises obtaining high molecular weight autologous urine isolates. These isolates are then injected into an immunologic organ such as the skin, with or without adjuvants known to potentiate an immune response. The invention also provides a method of treating cancer in a mammal in need of such treatment which comprises obtaining high molecular weight autologous urine isolates that are used to pulse antigen presenting cells such as dendritic cells that are then injected into the mammal.

The high molecular weight isolate from the urine of the mammal contains organism-specific tumor associated antigens and cachexia-inducing molecules, which, when injected into an immunogenic organ such as the skin, with or without an adjuvant will result in an immune response against the antigen and against the molecules that cause cachexia. Injection of dendritic cells that have been co-cultured with autologous high molecular weight isolates from the urine of the mammal with cancer will result in the processing of tumor antigens and cachexia-inducing molecules by the dendritic cells, and presentation of said antigens and molecules to the immune system of the mammal. This presentation will elicit an immune response by the T lymphocytes, which will proliferate and selectively attack tumor tissue and cells producing cachexia-inducing molecules.

The treatments can be performed without costly identification of specific tumor associated antigens, are without serious side effects, can halt cachexia, have a lower likelihood of inducing escape of variant tumor cells, and are potentially useful for a much larger percentage of the population than other immunotherapies which use single, non-autologous molecules, or tumor cell lysates as antigen sources.

Thus, this invention provides a novel, individualized, non-toxic method for the treatment of cancer and cancer and AIDS-induced cachexia.

DETAILED DESCRIPTION OF THE INVENTION

As used herein, "APC" is an antigen presenting cell of the immune system of mammals.

As used herein, "DC" is a dendritic cell, heretofore the most potent type of antigen presenting cell of the immune system of mammals.

As used herein, "HIU" is a high molecular weight isolate of urine.

As used herein, "UPDC" is HIU pulsed dendritic cell therapy.

As used herein, "antigen" is a molecule which will induce an immune response.

As used herein, "cachexia" is wasting, including weight loss occurring in the course of the disease cancer.

As used herein, "T lymphocyte" is an immune white blood cell which develops in the thymus, and is responsible for cell-mediated immunity.

As used herein, "pulse" is contact of antigen or cachexia-inducing molecule and dendritic cells.

As used herein, "reinfuse" is reintroduction into the corpus by means of a hypodermic needle, and may include intravenous, intramuscular, and subcutaneous routes.

The present invention is directed to the use of autologous HIU to elicit an immune response against cancer cells and cells producing cachexia-inducing molecules. In particular, the invention stems from the discovery that a type of antigen presenting cell, DCs pulsed with an autologous HIU:
1. Induce T lymphocyte mediated cytotoxicity of human tumor cells in vitro as effectively as dendritic cells pulsed with a target cell membrane derived antigen;
2. Halt cachexia when reinfused in a patient with advanced cancer; and
3. Result in regression of cancer in humans.

High Molecular Weight Isolate of Urine

The present invention contemplates the use of an isolate of autologous urine with a molecular weight of greater than about 1000 daltons as an effective pulsing agent for autologous dendritic cells and as an effective antigen source for direct injection into an immunogenic organ such as the skin. As used herein, the term "high molecular weight isolate of urine" (HIU) refers to any isolate of urine having a molecular weight of greater than about 1000 daltons.

The high molecular weight isolate of urine is derived by collecting the urine of a mammal for a period of time. The urine is first filtered, if required, to remove any particulate matter and then concentrated using a suitable concentrating method, and the high molecular weight components are separated from the lower molecular weight components by an appropriate method.

The low molecular weight components of urine are comprised of inorganic (salts, minerals, metals), nitrogenous compounds (urea, creatinine, creatine, guanidine, ammonia, alpha amino nitrogen, free amino acids, betaines, nitrites, aliphatic amines, aromatic amines, porphyrins and related products, purines and related compounds, nucleosides, cyclic nucleotides, uric acid, allantoin, and pyrimidines and related compounds), carbohydrates, lipids, organic acids, bile acids, prostaglandin, hormones, and vitamin molecules. Many of these molecules, which have no tumor associated antigenicity. In addition, they may competitively inhibit the interaction of unspecified tumor associated antigens found in the high molecular weight fraction of urine with the DCs and adversely affect the viability of the DCs at the time of pulsing. Therefore it is advantageous to remove these compounds.

It was found that removing molecules with a molecular weight of less than about 1000 daltons from a urine sample sufficiently concentrates the tumor associated antigens in the high molecular weight fraction so that effective pulsing of the DCs can take place. However, removal of further molecular weight fractions can produce an HIU that is as good or better.

For example, for an anti-tumor HIU, preferably molecules of molecular weight less than about 3,000 are removed, even more preferably, molecules less than about 10,000 are removed, more preferably molecules less than about 100,000 are removed and even more preferably molecules less than about 68,000 are removed. Alternatively, a 3 kd membrane is used to filter the urine, the retentate is saved and passed through a column that selectively binds albumin, and the filtrate is used as an antigen source.

For an anti-cachexia HIU, molecules less than about 1,000 and greater than about 60,000, more preferably, molecules less than about 10,000 and greater than about 30,000 are removed. One method, using currently available off-the-shelf filters is to first pass the urine through a 30 or 50 kd membrane, then pass the filtrate through a 10 kd membrane. Passing the 30 or 50 kd membrane removes the albumin and higher molecular weight antigens that could interfere with the antigenicity of the cachexia antigen and passing through the 10 kd membrane allows for removal of all of the junk. However, a 5 kd, 1 kd, or 500 Dalton membrane is equally effective, but may require a longer time for filtration.

In one embodiment, the less desirable molecular weight fractions are removed by filtration using different sized filters. Because one of the advantages of the invention is that it is simple, quick and inexpensive, filtration is a particularly desirable method, although one of skill in the art would be able to substitute new or previously known methods of separation by molecular weight. For example, column chromatography can be used to separate by size. Alternatively, column chromatography can be used to separate by other properties, such as when specifically isolating the anti-tumor or anti-cachexia related molecules.

Preferably the anti-tumor antigens/molecules for the present invention are in the range of 10,000-1,000,000 MW, more preferably in the range of 40,000-100,000, and even more preferably in the range of 68,000-100,000 MW. In one alternative embodiment proteins such as human albumin (MW about 60,000) can be removed to ensure that albumin does not dilute the desirable antigens, or interfere with binding to them. In a further alternative embodiment, the low molecular weight components below 10,000 which are less desirable, are removed. Alternatively, because most of the anti-tumor antigens/molecules are glycoproteins, in a further alternative embodiment, lectin affinity columns can be used to isolate the anti-tumor antigens/molecules to be used in the present application.

Preferably, the anti-cachexia antigens/molecules of the present invention, tend to be in the range of 1,000-60,000, more preferably in the range of 10,000-40,000. In one embodiment, the anti-cachexia antigens/molecules are isolated from the anti-tumor antigens/molecules. This can be accomplished using one or a mixture of molecular weight separating methods and chromatography methods.

The tumor, cachexia, or dual-specific HIU, when isolated by any of the methods of the preferred embodiments can then be used as a vaccine by itself or mixed with a biologically acceptable diluent or adjuvant. Alternatively, an antigen presenting cell is then pulsed with the HIU, the antigen presenting cells are grown in tissue culture, and the media removed. The APC's themselves or exosomes from the APC's are then injected into the animal or patient.

The APCs that may be used according to the present invention include, but are not restricted to, DCs differentiated in culture from bone marrow precursor cells, which express the human surface marker CD34, or from mononuclear cells not expressing the human cell surface marker CD34 in the blood (Romani N, et al 1994 *J Exp Med,* 180:83-93; Romani N et al. 1996 *J Immunol Methods;* 196:137-51 and; Reddy et al. 1997, *Blood;* 90:3640-6), and precommitted DCs collected from peripheral blood (Greudenthal P. S. et al 1990 *Proc Natl Acad Sci* 87:7698-7702; Mehta-Damani, et al. 1994 *J Immunol* 153:996-1003; Thomas R. et al. 1993 *J. Immunol* 151: 6840-6852; and Cohen P A et al, 1997, U.S. Pat. No. 5,643, 786). The method of isolating or inducing large numbers of DC does not affect the invention. An amount of DC's sufficient to induce an immune response should be used.

Exosomes can be isolated from the media of the APC's which have been pulsed with the HIU. Exosomes are defined herein as small cell membrane fragments which, in this case, contain the necessary information to elicit a T-cell response, i.e.: co-stimulatory molecules and antigens or epitopes. In a preferred embodiment, the exosomes are harvested from the media of mature dendritic cells. When the exosomes are injected into animals, antitumor responses equal to or better than those induced by dendritic cells are seen. In a further embodiment, the pulsed antigen-presenting cells are themselves injected into the animal or patient.

In one embodiment, the method is used to treat all solid tumors, including sarcomas and carcinomas. In an alternative embodiment, the method is used to treat lymphomas and leukemias. In a further alternative embodiment, the method is used to treat the cachexia associated with AIDS.

The antigens in the form of dendritic cells which are pulsed with the antigens, exosomes, or the HIU itself, can be injected into the patient using any injection route, intravenous, subcutaneous, intradermal, or intralymphatic. Preferably, the antigens are injected intradermally or subcutaneously. Without being restricted to this theory, it is believed that the antigens are picked up by the langerhans cells which migrate to the lymph nodes. The antigens can be administered using more then one form. For example, the antigens may be administered as a mixture of pulsed dendritic cells and exosomes together or separately and alternating.

In a further embodiment, the isolate is administered in combination with an immune stimulating compound. There are many immune stimulating compounds which may be administered which are known to one of skill in the art, including, but not limited to, heat shock proteins and bacterial cell wall extracts.

Other cancer treatment methods known to one of skill in the art may be used in addition to the method disclosed herein. For example, in Example 9, the tumor shrinks to a size which is resectable. Alternatively, other chemotherapy method can be used in addition to, or alternating with the present method.

EXAMPLE 1

Isolation of HIU 1,000 to 10,000 mL of urine was collected from a human with cancer. The urine was first filtered to remove any particulate matter, and then placed in a CH2 concentrator (Millipore, USA) equipped with a 1,000 dalton filter cartridge (or an appropriately sized cartridge for one of the other embodiments). The retentate (in this case, containing molecules of >1,000 daltons size) was collected and the protein content of the retentate was calculated using an ultraviolet spectrometer. The retentate was then used as a vaccine or used to pulse the DCs of the same person from which the urine was collected. The resulting DCs or exosomes were then injected into the patient.

In a preferred embodiment of the invention for the treatment of cancer in mammals, DCs are propagated in the following way.

EXAMPLE 2

Isolation of Mononuclear Cells 50-100 ml of peripheral blood was collected in tubes containing the anticoagulant heparin and then transferred to Lymphoprep™ (Nycomed Pharma AS, Oslo, Norway) lymphocyte separation tubes. Centrifugation of these tubes concentrated peripheral blood mononuclear cells (PBMC) in a distinct band at the sample-medium interface. Alternatively, PBMCs were obtained by leukapheresis. PBMCs were then suspended at a concentration of $10^6$ cells/ml in OPTI-MEM tissue culture media (Gibco BRL, Gaithersburg, Md.), supplemented with 5% human serum and incubated in tissue culture plates or flasks treated to promote cell attachment. After ninety minutes incubation at 37° C., the non-adherent cells were removed and discarded.

EXAMPLE 3

Expansion of Dendritic Cell Population

The adherent mononuclear cells were cultured in OPTI-MEM supplemented with 500 U/ml granulocyte macrophage colony stimulating factor (GM-CSF, Pepro Tech Inc., Rocky Hill, N.J.) and 500 U/ml interleukin-4 (IL-4, Pepro Tech Inc., Rocky Hill, N.J.). GM-CSF and IL-4 are cytokines that have been shown to stimulate dendritic cell growth and antigen presenting capabilities. After four to six days growth, dendritic cells were collected by pipetting, leaving behind the tightly attached macrophages. They were then diluted threefold in cytokine supplemented media and transferred to new tissue culture flasks. Dendritic cells were then identified by one of the three following methods:

1. Light microscopy, identifying the unique morphology of dendritic cell colonies following the teaching of Romani, et al. (J. Exp Med, 1994 180:83-93).
2. Detection of Dendritic cells antigens by tagging with fluorescent antibodies and detection using a fluorescence microscope.
3. Detection of Dendritic cells antigens by tagging with fluorescent antibodies and detecting on a flow cytometer.

EXAMPLE 4

Pulsing Dendritic Cells with Antigen

After expansion, autologous dendritic cells were mixed with a solution containing the autologous high molecular weight urine isolate isolated as described above. The final protein concentration of the high molecular weight urine isolate used to pulse the dendritic cells was between about 1 and 2000 µg per ml. Preferably 200-400 µg per ml. After a period of between about 30 min and 24 hours, preferably about 6-12 hours, the solution containing dendritic cells and the high molecular weight urine isolate was centrifuged, and the supernatant discarded. The cells were then washed 2-3 times with 5-20 volumes of sterile saline, and resuspended in 100 ml of sterile normal saline for infusion, and the cells and sterile saline were intravenously infused into the patient from which they were originally isolated. Alternatively, the APCs were placed in a hypertonic solution containing the antigen and/or cachexia-inducing molecules for a period of time sufficient to result in osmotic lysis and resulting pinocytosis of the mixture by the APCs. The method of osmotic lysis is readily available and known to one of skill in the art.

EXAMPLE 5

Reinfusion of Dendritic Cells

The DCs were infused into the patient using an injection route, either intravenous, subcutaneous, intradermal, or intralymphatic. Preferably, the DC's were injected over or into inguinal lymph nodes or inguinal lymph beds. DC's can be injected intradermally, but required the dendritic cells to have to cross basement membranes, suggesting intralymphatic injections are preferable.

EXAMPLE 6

Resolution of Cachexia in a Patient Diagnosed with Terminal Prostate Cancer 1,000 to 10,000 mL of urine were collected from a human with end-stage metastatic prostate cancer. The urine was first filtered to remove any particulate matter, and then placed in a CH2 concentrator (Millipore, USA) equipped with a 1,000 dalton filter cartridge. The retentate (containing molecules of >1,000 daltons size) was collected. The protein content of the retentate was calculated using an ultraviolet spectrometer.

The high molecular weight isolate from a patient with end-stage metastatic prostate cancer was isolated as described. Dendritic cells were isolated from 80 ml of peripheral blood from the same patient and expanded as described in Example 3. Prior to receiving therapy, the 78 year old patient had failed multiple treatments including standard chemotherapy, multiple surgeries, hormone ablation therapy, and multiple radiation treatments for his prostate cancer. He was also losing weight rapidly. In the 3 months prior to therapy, his weight had decreased by 42 lbs. Prior to therapy, the patient required frequent (every 3-7 days) intravenous infusions of packed red blood cells to correct anemia which was secondary to profuse urinary bleeding from prostate tumor infiltrating the bladder.

His dendritic cells were exposed to a high molecular weight urine isolate, and the exposed dendritic cells were reinfused into his vein as described above.

One month after the first infusion, the patient's weight had increased by 6.5 lbs, and no packed red blood cell infusions were required because the bleeding had slowed to a point where the patients red blood cell indices began to rise.

EXAMPLE 7

Induction of Lymphocyte Stimulation and Increased Interferon Gamma Production by Dendritic Cells Pulsed with HIU Human DCs were pulsed with HIU from a human with metastatic colon cancer as described in Example 4. The DCs were then co-cultured with human lymphocytes. An ELISPOT assay for interferon-gamma was then performed on control lymphocytes as well as those co-cultured with the pulsed DCs. An average of four stimulated lymphocytes per well were measured in wells containing treated lymphocytes compared to an average of one stimulated lymphocytes per well for the controls, corresponding to a 400% increase ($p<0.05$).

EXAMPLE 8

Induction of T Lymphocyte Proliferation by Dendritic Cells Pulsed with HIU

Samples of human DCs prepared as above. They were pulsed using osmotic lysis as described above with either HIU from a human with metastatic colon cancer or with an equal concentration by weight of tumor cell lysate of the target tumor cell line, SW620 (human colon cancer cell line obtained from ATCC, Rockville, Md.). The DC's were cultured a further 3 days in the presence of 30% monocyte conditioned medium that was obtained by culturing human monocytes in RPMI 1640 culture medium in the presence of gamma globulin for a period of 2 days. The dendritic cells were then co-cultured with lymphocytes collected from the same donor as the monocytes for the DC preparation. After a period of time, the lymphocyte/DC mixture was co-cultured with target tumor cells containing an intracellular marker that, when detected outside the cell serves as a marker for lysis of the tumor cells. Methods for the measurement of tumor cell lysis are known to those skilled in the art. The amount of specific lysis (total tumor cell lysis minus non-specific lysis of tumor cells by control dendritic cell/lymphocyte preparations) was then calculated.

The specific lysis of tumor cells using lymphocytes/DCs pulsed with urine antigen was 18.77% versus 12.11% of the lymphocytes/DCs pulsed with tumor lysate antigen (n=9), demonstrating that urine antigen results in as good as, and apparently better, stimulation of cell mediated immunity toward tumor cells than even the antigens of the tumor cells themselves.

EXAMPLE 9

Treatment of a Patient Diagnosed with Neuroblastoma

A 14 year old male was diagnosed with an intracranial neuroblastoma at age 8. Despite conventional therapy, the tumor was never eradicated and continued to grow. The patient was confined to a wheelchair secondary to the growing tumor. The patient was treated with dendritic cells pulsed with autologous urine antigen as described in Examples 1-4. He was given weekly injections of dendritic cells and exosomes for four weeks. After the third injection, the patient was able to walk unassisted. After the fourth injection, the patient was able to climb stairs. A CT-scan after the fourth injection revealed the tumor was approximately 20% smaller than prior to the beginning of the injections. After the sixth injection, the tumor was 40% smaller than baseline, he was able to stop taking hydrocortisone and was able to have the previously unresectable tumor surgically resected.

EXAMPLE 10

Treatment of a Patient Diagnosed with Renal Cell Carcinoma

A 27 year old Caucasian female with primary renal cell carcinoma with metastases to the bones (right pubic ramus, right first and second ribs) and cervical and supraclavicular lymph nodes resulting in prominent lymphadenopathy was treated with dendritic cells and exosomes prepared as in Examples 1-4—dendritic cells being pulsed with autologous HIU. The treatment schedule was injections of dendritic cells and exosomes weekly on weeks 1, 2, 3, 4, 8, and 12. After the twelve week injection cervical and supraclavicular adenopathy resolved. No resolution of the primary mass or bone metastases was seen.

EXAMPLE 11

Treatment of a Patient Diagnosed with Metastatic Renal Cell Carcinoma

A 71 year old Caucasian male with renal cell carcinoma metastatic to the thyroid gland, mediastinum and bones was treated with dendritic cells and exosomes prepared as in examples 1-4—dendritic cells were pulsed with autologous HIU. After 4 weekly injections of dendritic cells and exosomes, the mediastinal metastases had reduced in size by 40% and 80% of the bone metastases had resolved.

EXAMPLE 12

Treatment of a Patient Diagnosed with Adenocarcinoma

A 37 year old Caucasian female with infiltrating ductal adenocarcinoma of the left breast with localized spread to the axillary lymph nodes was treated with dendritic cells and exosomes prepared by harvesting the media from the growing dendritic cells pulsed with autologous HIU (isolated as described in Example 1). After 2 weekly injections of dendritic cells and exosomes, the primary tumor mass and the axillary adenopathy decreased by approximately 30%.

EXAMPLE 13

Treatment of a Patient Diagnosed with Ductal Carcinoma of the Breast

A 48 year old Caucasian female with ductal carcinoma of the left breast with metastases to the bones, and lungs was treated with dendritic cells and exosomes prepared as described—dendritic cells were pulsed with autologous HIU (prepared as in Example 1). After 4 weekly injections of dendritic cells and exosomes, 70% of the bone metastases had resolved and the lung metastases were reduced in size by approximately 60%.

EXAMPLE 14

Treatment of a Patient Diagnosed with Carcinoma of the Ureter

A 74 year old Caucasian male with transitional cell carcinoma of the left ureter with inguinal and periaortic lymph node adenopathy and metastatic spread was treated with dendritic cells and exosomes prepared as above—dendritic cells were pulsed with autologous HIU. After 4 weekly injections of dendritic cells and exosomes, the inguinal and periaortic adenopathy had resolved, and the primary tumor at the uretocystic junction was reduced in size by 45%.

EXAMPLE 15

Treatment of a Patient Diagnosed with Carcinoma of the Rectum

A 49 year old Caucasian male with squamous cell carcinoma of the rectum was treated with dendritic cells and exosomes prepared as above—dendritic cells were pulsed with autologous HIU. After 5 weekly injections of dendritic cells and exosomes, the rectal mass decreased in size from 78 mm to 42 mm at its greatest diameter.

EXAMPLE 16

Treatment of Cachexia in a Patient Diagnosed with AIDS

Dendritic cells pulsed with HIU from a cancer patient, the HIU alone, or exosomes from the growth of the Dendritic cells are prepared using the method disclosed herein. Then 2-10 weekly injections are administered until the patient stops losing weight or begins to gain weight.

EXAMPLE 17

Treatment of a Patient Diagnosed with a Sarcoma

Dendritic cells pulsed with HIU from a patient diagnosed with a sarcoma, the HIU alone, or exosomes from the growth of the Dendritic cells are prepared using the method disclosed herein. Then 2-10 weekly injections are administered until the sarcoma regresses partially or completely or slows in growth.

EXAMPLE 18

Treatment of a Patient Diagnosed with a Lymphoma

Dendritic cells pulsed with HIU from a patient diagnosed with a sarcoma, the HIU alone, or exosomes from the growth of the Dendritic cells are prepared using the method disclosed herein. Then 2-10 weekly injections are administered until the sarcoma regresses partially or completely or slows in growth.

What is claimed is:

1. A method for reducing the size of a carcinoma in a mammal, comprising:
   collecting urine from a mammal with carcinoma;
   preparing an isolate comprising a pool of molecules larger than about 1000 daltons from said urine;
   pulsing dendritic cells with said isolate, wherein said isolate is in a solution at a concentration of between 200-400 µg per ml; and
   reinfusing an effective amount of the dendritic cells into said mammal with carcinoma;
   wherein said carcinoma is selected from the group consisting of: renal cell carcinoma, carcinoma of the breast, carcinoma of the ureter and rectal carcinoma.

2. The method of claim 1, wherein said dendritic cells are allogeneic dendritic cells.

3. The method of claim 1 wherein said reinfusing is selected from the group consisting of intra-muscular, intra-venous, intradermal, subcutaneous, and intralymphatic.

4. The method of claim 1 wherein said reinfusing is into the tumor itself.

5. The method of claim 1 wherein said mammal is a human.

6. The method of claim 1 wherein said preparation of said isolate comprises:
   collecting about 1,000 to about 10,000 mls of urine from said mammal with carcinoma,
   filtering the urine to remove particulate matter, and
   concentrating the proteins larger than about 1,000 daltons.

7. The method of claim 6 wherein said concentrating comprises placing the filtered urine in a concentrator equipped with a 1,000 dalton filter cartridge.

8. The method of claim 1, wherein said isolate comprises molecules larger than about 5,000 daltons.

9. The method of claim 1, wherein said isolate comprises molecules larger than about 10,000 daltons.

10. The method of claim 9, wherein said isolate comprises molecules smaller than about 60,000 daltons.

11. The method of claim 1, wherein said isolate comprises molecules larger than about 100,000 daltons.

12. The method of claim 1, wherein said isolate comprises molecules larger than about 1,000 and smaller than about 1,000,000 daltons.

13. The method of claim 1, wherein said isolate comprises molecules larger than about 3,000 and smaller than about 100,000 daltons.

14. The method of claim 1, wherein said isolate comprises molecules larger than about 10,000 and smaller than about 50,000 daltons.

15. The method of claim 1, wherein said isolate is administered within exosomes.

16. The method of claim 15, wherein said exosomes are obtained from APCs which are co-cultured with said isolate.

17. The method of claim 16, wherein the APCs are from the mammal being treated.

18. The method of claim 1, wherein said effective amount of APCs or exosomes are washed APCs or washed exosomes.

19. The method of claim 13, wherein said isolate comprises molecules larger than about 40,000 and smaller than about 100,000 daltons.

20. The method of claim 13, wherein said isolate comprises molecules larger than about 68,000 and smaller than about 100,000 daltons.

21. The method of claim 1, wherein said pulsing comprises:
   incubating said dendritic cells with said solution of isolate for a period of about 6-12 hours; and
   resuspending said dendritic cells in 100 ml of sterile saline.

22. The method of claim 1, further comprising obtaining dendritic cells by the method comprising:
   isolating peripheral blood mononuclear cells (PBMC) from 50-100 ml of peripheral blood from said mammal;
   incubating said PBMC in tissue culture media to yield a population of adherent mononuclear cells; and
   collecting dendritic cells from said population of adherent mononuclear cells by pipetting to separate dendritic cells from tightly attached macrophage cells.

* * * * *